(12) United States Patent
Hoffmann et al.

(10) Patent No.: US 7,863,474 B2
(45) Date of Patent: Jan. 4, 2011

(54) PROCESS FOR THE PREPARATION OF CETP(1)

(75) Inventors: Ursula Hoffmann, Muttenz (CH); Bruno Lohri, Reinach BL (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/474,328

(22) Filed: May 29, 2009

(65) Prior Publication Data
US 2009/0240080 A1    Sep. 24, 2009

Related U.S. Application Data

(63) Continuation of application No. 11/951,444, filed on Dec. 6, 2007, now abandoned.

(30) Foreign Application Priority Data
Dec. 20, 2006   (EP) .................................. 06126724

(51) Int. Cl.
*C07C 327/00* (2006.01)
*C07C 61/08* (2006.01)

(52) U.S. Cl. ...................................... 558/230; 562/400

(58) Field of Classification Search ................. None
See application file for complete search history.

(56) References Cited

U.S. PATENT DOCUMENTS
2003/0092708 A1    5/2003    Shinkai et al.

FOREIGN PATENT DOCUMENTS
EP    1 020 439    7/2000

OTHER PUBLICATIONS

Shinkai et al., J. Med. Chem, 43, pp. 3566-3572 (2000).
Creger, P.L., Ann. Rep. Med. Chem., 12, pp. 278-287 (1977).
Petragnani et al., Synthesis, pp. 521-578 (1982).
Roth et al., J. Med. Chem., vol. 35, No. 9, pp. 1609-1617 (1992), XP002437815.
Creger, P.L., J. Am. Chem. Soc., vol. 92, No. 5, pp. 1397-1398 (1970), XP002437816.

*Primary Examiner*—Paul A Zucker
(74) *Attorney, Agent, or Firm*—George W. Johnston; Dennis P. Tramaloni; Brian C. Remy

(57) ABSTRACT

The present invention relates to a process for the preparation of 1-(2-ethyl-butyl)-cyclohexanecarboxylic acid which is useful as an intermediate in the preparation of pharmaceutical active compounds.

17 Claims, No Drawings

PROCESS FOR THE PREPARATION OF CETP(1)

PRIORITY TO RELATED APPLICATION(S)

This application is a continuation of U.S. application Ser. No. 11/951,444, filed Dec. 6, 2007, now abandoned, which claims the benefit of European Patent Application No. 06126724.1, filed Dec. 20, 2006. The entire contents of the above-identified applications are hereby incorporated by reference.

BACKGROUND OF THE INVENTION

The present invention relates to a process for the preparation of 1-(2-ethyl-butyl)-cyclohexanecarboxylic acid which is useful as an intermediate in the preparation of pharmaceutical active compounds.

SUMMARY OF THE INVENTION

In a first aspect, the present invention provides a process for the preparation of 1-(2-ethyl-butyl)-cyclohexanecarboxylic acid of formula (I):

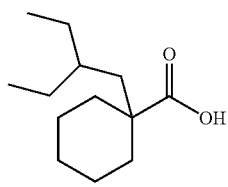

(I)

which comprises reacting a cyclohexanecarboxylic acid derivative of formula (II):

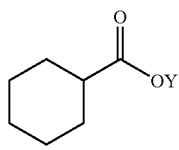

(II)

wherein Y is an alkali metal, with an alkylating agent (such as a 1-halo-2-ethylbutane or a sulfonate ester of 2-ethyl-1-butanol), in the presence of a secondary amine and $(C_1-C_6)$alkyllithium, $(C_3-C_6)$cycloalkyllithium or phenyllithium.

The compound of formula (I) may be used as an intermediate in the synthesis of valuable pharmaceutical compounds, such as the ones described in EP1,020,439.

DETAILED DESCRIPTION OF THE INVENTION

Unless otherwise stated, the following terms used in the specification and claims have the meanings given below:

The term "halo" means chloro, bromo or iodo.

The term "alkali metal" includes lithium, sodium, potassium, rubidium and cesium. Preferably, alkali metal is lithium or sodium. Of these, sodium is most preferred.

The term "$(C_1-C_6)$alkyl" refers to a branched or straight hydrocarbon chain, such as methyl, ethyl, n-propyl, isopropyl, n-butyl, isobutyl, sec-butyl and t-butyl, pentyl, or hexyl.

The term "$(C_3-C_6)$cycloalkyl" refers to a single saturated carbocyclic ring, such as cyclopropyl, cyclobutyl, cyclopentyl and cyclohexyl.

The term "$(C_1-C_6)$alkyllithium" refers to a $(C_1-C_6)$alkyl chain as defined above which is substituted by a lithium atom, such as butyllithium, hexyllithium, or sec-butyllithium.

The term "$(C_1-C_6)$alkoxy" refers to a —O—$(C_1-C_6)$alkyl wherein the $(C_1-C_6)$alkyl is as defined above. Examples of a $(C_1-C_6)$alkoxy include methoxy, ethoxy, and isopropoxy.

The term "substituted phenyl" refers to a phenyl substituted by one or more substituents independently selected from the group consisting of a $(C_1-C_3)$alkyl, nitro and a halogen atom (such as fluoro, bromo, chloro).

The term "secondary amine" refers to an amine of formula (a)

(a)

where $R^1$ and $R^2$ may be the same or different and are independently either a $(C_1-C_6)$alkyl or $(C_3-C_6)$cycloalkyl, or $R^1$ and $R^2$ taken together with the nitrogen atom to which they are attached, form a $(C_4-C_8)$heterocycloalkane optionally containing an additional heteroatom of O or N. Representative examples of secondary amines include, but are not limited to, piperidine, 4-methyl-piperidine, piperazine, pyrrolidine, morpholine, dimethylamine, diethylamine, diisopropylamine, dicyclohexylamine, ethylmethylamine, ethylpropylamine and methylpropylamine. Preferably, the secondary amine is diethylamine, diisopropylamine, dicyclohexylamine, ethylmethylamine, ethylpropylamine, methylpropylamine or morpholine. The most preferred secondary amine is diethylamine.

The term "$(C_4-C_8)$heterocycloalkane" refers to a saturated non-aromatic cyclic compound of 4 to 8 ring atoms in which one or two ring atoms are heteroatoms independently selected from N or O, and wherein the heterocycloalkane may be optionally substituted with one or more $(C_1-C_3)$alkyls [preferably one $(C_1-C_3)$alkyl].

The term "sulfonate ester of 2-ethyl-1-butanol" refers to a substituted or an unsubstituted phenyl-sulfonate, an unsubstituted naphthalene-sulfonate or a $(C_1-C_6)$alkylsulfonate ester derivative of 2-ethyl-1-butanol wherein the substituted phenyl and the $(C_1-C_6)$alkyl chain are as previously defined. Representative examples of sulfonate ester of 2-ethyl-1-butanol include, but are not limited to, benzenesulfonic acid 2-ethyl-butyl ester, 1-naphthalenesulfonic acid 2-ethyl-butyl ester, 2-naphthalenesulfonic acid 2-ethyl-butyl ester, toluene-4-sulfonic acid 2-ethyl-butyl ester, 4-nitro-benzenesulfonic acid 2-ethyl-butyl ester, 2,4,6-trimethyl-benzenesulfonic acid 2-ethyl-butyl ester, ethanesulfonic acid 2-ethyl-butyl ester, methanesulfonic acid 2-ethyl-butyl ester and butanesulfonic acid 2-ethyl-butyl ester.

In reference to a particular group or molecule, the term "substituted" refers to the fact that at least one of the hydrogen atoms of that group or molecule is replaced by some other substituent.

The present invention is also directed to a process for the preparation of 1-(2-ethyl-butyl) cyclohexanecarboxylic acid of formula (I):

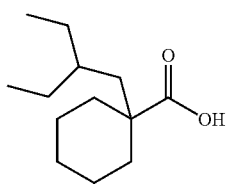

which comprises the following steps:

a) alkylating a cyclohexanecarboxylic acid derivative of formula (II):

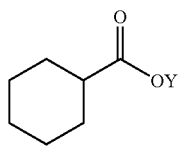

wherein Y is an alkali metal, with an alkylating agent, in the presence of a secondary amine and a $(C_1-C_6)$alkyllithium, a $(C_3-C_6)$cycloalkyllithium or phenyllithium, and b) purifying the compound of formula (I) by extraction with an aqueous solution with a pH in the range of 7.5-11.

In another embodiment, the present invention is directed to a process for the preparation of 1-(2-ethyl-butyl)cyclohexanecarboxylic acid of formula (I):

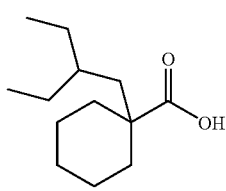

which comprises the following steps:

a) reacting cyclohexanecarboxylic acid with a basic alkali metal compound, such as an alkali metal hydride (e.g. NaH, KH), an alkali metal amide (e.g. NaNH$_2$, LiNH$_2$), an alkali metal alkoxide (e.g, NaOMe, LiOMe, NaOEt, LiOEt, KOEt, NaOiPr, KOiPr), an alkali metal hydroxide (e.g. LiOH, NaOH, KOH), an alkali metal carbonate (e.g. Na$_2$CO$_3$, K$_2$CO$_3$, Cs$_2$CO$_3$) or an alkali metal hydrogen carbonate (e.g. NaHCO$_3$, KHCO$_3$) to form a cyclohexanecarboxylic acid alkali salt of formula (II):

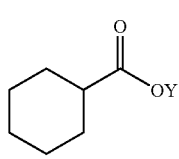

wherein Y is an alkali metal;

b) reacting the said cyclohexanecarboxylic acid alkali salt with an alkylating agent, in the presence of a secondary amine and $(C_1-C_6)$alkyllithium, $(C_3-C_6)$cycloalkyllithium or phenyllithium; and c) purifying the compound of formula (I) by extraction with an aqueous solution with a pH in the range of 7.5-11.

According to the present invention, the preferred alkali metal compound is sodium hydride when the above steps a), b) and c) are carried out as a one-pot synthesis.

Preferably, $(C_1-C_6)$alkyllithium, $(C_3-C_6)$cycloalkyllithium or phenyllithium is added first to the cyclohexanecarboxylic acid alkali salt of formula (II), in the presence of a secondary amine, followed by the addition of an alkylating agent.

According to the present invention, the preferred alkali metal compound used is sodium hydroxide or sodium methoxide. Sodium methoxide is the most preferred alkali metal compound.

The present invention takes place in the presence of an organic solvent such as an ether like solvent (e.g. tetrahydrofuran, diisopropyl ether, t-butylmethyl ether or dibutyl ether), an alcohol solvent (e.g. methanol or ethanol), an aliphatic hydrocarbon solvent (e.g. hexane, heptane or pentane), a saturated alicyclic hydrocarbon solvent (e.g. cyclohexane or cyclopentane) or aromatic solvent (e.g. toluene or t-butylbenzene).

In addition to the solvents previously listed, the purification step, may take place in the presence of a chlorinated solvent (e.g. methylene chloride or chloroform), or a mineral solvent (water).

A nonprotic organic solvent is the preferred solvent during the alkylation, such as tetrahydrofuran, alone or in combination with another nonprotic solvent, e.g. from the group of the apolar solvents hexane, heptane and t-butyl-benzene. Most preferably the nonprotic solvent is tetrahydrofuran.

Preferably, the present invention takes place in the presence of catalytic amount of a secondary amine.

The present process is preferably carried out with 0.05 to 1.0 equivalent, more preferably with 0.1 to 0.3 equivalent of a secondary amine with respect to the cyclohexanecarboxylic acid alkali salt of formula (II). Most preferably 0.1 equivalent of a secondary amine with respect to the compound of formula (II) is used.

The preferred lithium agent is $(C_1-C_6)$alkyllithium, and butyllithium is the most preferred.

1 to 1.3 equivalents of butyllithium with respect to cyclohexanecarboxylic acid alkali salt of formula (II) are preferably used for the alkylation steps. More preferably, 1.1 to 1.2 equivalents are used. Most preferably 1.2 equivalents are used.

According to the present invention, additional $(C_1-C_6)$ alkyllithium may be added to the reaction mixture after the alkylating step and prior to the extraction.

The preferred aqueous solution for the extraction step has a pH within the range of 7.5-10, more preferably 8.5-9.5 and most preferably has a pH of 9.

According to the present invention the aqueous solution for the extraction step is preferably chosen from inorganic bases or organic bases, a mixture thereof, or from commonly known buffering solutions of suitable pH. The preferred inorganic base is an alkali base, such as alkalicarbonate, alkalibicarbonate, alkali-borate, alkali phosphate, alkali-hydroxide. A more preferred aqueous solution is chosen from solution of potassium bicarbonate, sodium bicarbonate, potassium carbonate, sodium carbonate, sodium borate, sodium hydroxide, or a mixture thereof. The most preferred aqueous solution is a solution of sodium bicarbonate, sodium hydroxide or a mixture thereof.

The preferred concentration of the butyllithium solution is 1.6 to 2.5M, more preferably 1.6M.

The preferred temperature for the addition of BuLi is 15-40° C. The most preferred temperature for the addition of butyllithium is 20-25° C.

Preferably the butyllithium is added over a 1 to 5 hour period, most preferably 3-4 hours.

The preferred alkylating agent is 1-halo-2-ethylbutane, most preferably 1-bromo-2-ethylbutane.

The preferred sulfonate ester of 2-ethyl-1-butanol is toluene-4-sulfonic acid 2 ethyl-butyl ester.

Preferably 1.2 equivalents of 1-bromo-2-ethylbutane are used.

The preferred addition temperature of 1-bromo-2-ethylbutane is 8-12° C.

The reaction time takes 5 to 24 hours, preferably 6 to 7 hours.

Preferably the alkylating agent is added to the reaction mixture immediately after the complete addition of alkyllithium, at a temperature between 8-12° C.

The preferred reaction temperature, once the addition of the alkylating agent is completed, is between 0 and 40° C., most preferably it is between 33 and 37° C.

The alkylation is performed preferably under an inert gas atmosphere, preferably under argon or nitrogen.

In another embodiment the present invention provides a process comprising the synthetic steps represented in the following scheme:

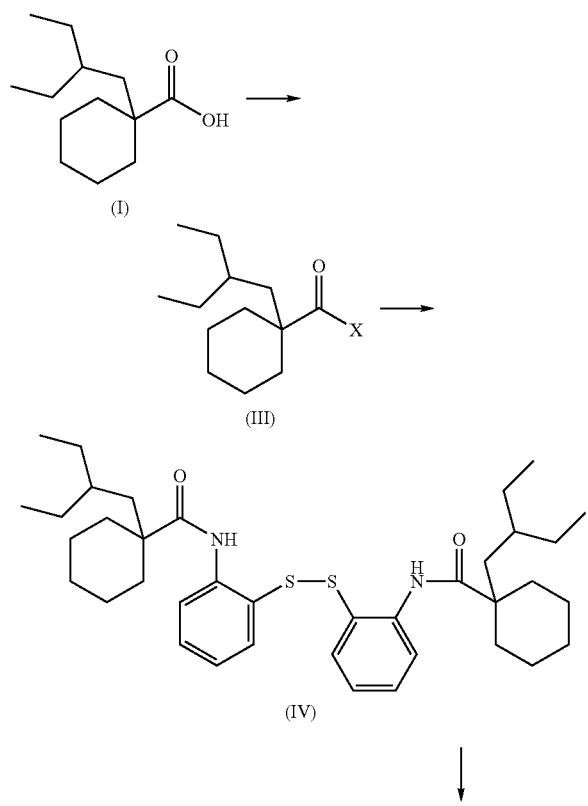

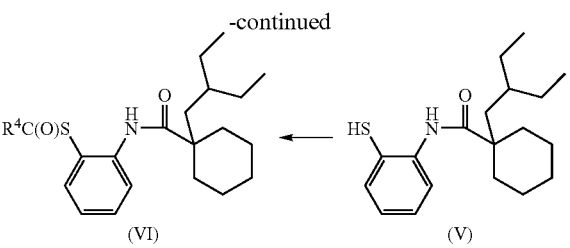

wherein X is I, Br, Cl or F and $R^4$ is $C_1$-$C_8$alkyl. In particular, the process comprises reacting 1-(2-ethyl-butyl)-cyclohexanecarboxylic acid (I) with a halogenating agent, such as $PX_3$, $PX_5$, $SOX_2$ or NCX, to obtain the acyl halide of formula (III). The halogenating step is preferably carried out in the presence of tri-($C_1$-$C_5$)alkylamine. Furthermore, the process comprises reacting the acyl halide with bis(2-aminophenyl) disulfide to acylate the amino groups of the (2-aminophenyl) disulfide, reducing the amino-acylated disulfide product with a reducing agent such as triphenylphosphine, zinc or sodium borohydride to yield the thiol product, and acylating the thiol group in the thiol product with $R^4C(O)X'$, wherein X' is I, Br, Cl or F.

The additional steps may be performed according to the procedures described in Shinkai et al., J. Med. Chem. 43:3566-3572 (2000) and WO 2007/051714.

Preferably the halogenating agent is chosen from thionyl chloride, phosphorus pentachloride, phosphorus tribromide and cyanuric fluoride, most preferably thionyl chloride. The acyl halide of formula (III) wherein X is Cl is most preferred.

In the thiol acylation step, preferably the acylating agent is $R^4C(O)X'$, wherein X' is Cl. Most preferably $R^4$ is isopropyl.

In a further embodiment the present invention provides a process for the preparation of S-[2-([[1-(2-ethylbutyl)-cyclohexyl]-carbonyl]amino)phenyl]2-methylpropanethioate comprising the formation of a compound of formula (I) obtained by any of the processes and conditions mentioned previously.

The following examples are provided for the purpose of further illustration and are not intended to limit the scope of the claimed invention.

The following abbreviations and definitions are used: br (broad); BuLi (butyllithium); $CDCl_3$ (deuterated chloroform); CHCA Li salt (cyclohexanecarboxylic acid lithium salt); CHCA Na salt (cyclohexanecarboxylic acid sodium salt); DCM (dichloromethane); DEA (diethylamine); eq. (equivalent); g (gram); GC (gas chromatography); h (hour); HCl (hydrochloric acid); M (Molar); m (multiplet); Me (methyl); MeOH (methanol); mL (milliliter); NMR (nuclear magnetic resonance); PhLi (phenyllithium); RT (room temperature); s (singlet); t (triplet); TBME (t-butyl methyl ether); and THF (tetrahydrofuran);

EXAMPLE 1

Preparation of CHCA Na Salt

At 5-10° C., a solution of cyclohexanecarboxylic acid (25.0 g, 195 mmol) in MeOH (75 mL) was added dropwise over 30 min to 5.4 M sodium methoxide (36.1 mL, 195 mmol) which had been diluted with MeOH (50 mL). The mixture was stirred 4 h at RT. Heptane (100 mL) was added dropwise. From the suspension thus formed most of the MeOH was removed in a rotary evaporator. Heptane (150 mL) was added and the white suspension was stirred 2 h at 0° C. and filtered.

The filter cake was washed with heptane and dried to afford 27.41 g (94%) CHCA Na salt as white crystals. Anal. Calcd for $C_7H_{11}NaO_2$ C, 55.99; H, 7.38. Found: C, 55.69; H, 7.25.

EXAMPLE 2

Alkylation of CHCA Na Salt in the Presence of Diisopropylamine (0.3 eq)

CHCA Na salt (2.34 g, 15.6 mmol) was suspended under argon in THF (30 mL). Diisopropylamine (474 mg, 4.68 mmol) was added to the stirred mixture followed by addition of 1.6 M BuLi in hexane (13.6 mL, 21.8 mmol) over 1.5 h using a syringe pump. After complete BuLi addition stirring at RT was continued for 1.5 h. 1-Bromo-2-ethylbutane (3.35 g, 20.3 mmol) in THF (10 mL) was added dropwise to the orange and slightly turbid reaction mixture at ~0° C. over 10 min. After 1 h the cooling bath was removed and the white suspension was stirred 18 h at ambient temperature. GC analysis indicated the presence of 7% unreacted starting material. An additional portion of 1.6 M BuLi in hexane (2.9 mL, 4.6 mmol) was added over 1 h to the reaction mixture and stirring at room temperature was continued for another 3 h.

At 5° C., ice-cold $H_2O$ (15 mL) was cautiously dropped to the reaction mixture under stirring. Then hexane and $H_2O$ were added and the mixture was concentrated in vacuo until most of the THF was removed. The residue was extracted with hexane (2×60 mL). The organic phases were washed with $H_2O$. The aqueous phases were combined, adjusted to ~pH 2 with aqueous HCl and extracted with DCM (2×100 mL). The dichloromethane phases were washed with dilute brine, dried over sodium sulfate and concentrated in vacuo to give 2.75 g crude product with a content of 5.4% cyclohexanecarboxylic acid and 83.9% 1-(2-ethyl-butyl)-cyclohexanecarboxylic acid corresponding to a yield of 70%.

EXAMPLE 3

Alkylation of CHCA Na Salt in the Presence of Diisopropylamine (0.1 eq)

CHCA Na salt (2.34 g, 15.6 mmol) was suspended under argon in THF (30 mL). Diisopropylamine (158 mg, 1.56 mmol) was added to the stirred mixture followed by addition of 1.6 M BuLi in hexane (11.2 mL, 17.9 mmol) over 2 h using a syringe pump. After complete BuLi addition stirring at RT was continued for 1.5 h. 1-Bromo-2-ethylbutane (3.35 g, 20.3 mmol) in THF (10 mL) was added dropwise to the orange and slightly turbid reaction mixture at ~0° C. over 10 min. After 1 h the cooling bath was removed and the white suspension was stirred 18 h at ambient temperature.

At 5° C., ice-cold $H_2O$ (15 mL) was cautiously dropped to the reaction mixture under stirring. Then hexane and $H_2O$ were added and the mixture was concentrated in vacuo until most of the THF was removed. The residue was extracted with hexane (2×60 mL). The organic phases were washed with $H_2O$. The aqueous phases were combined, adjusted to ~pH 2 with aqueous HCl and extracted with DCM (2×100 mL). The dichloromethane phases were washed with dilute brine, dried over sodium sulfate and concentrated in vacuo to give 2.7 g crude product with a content of 4.7% cyclohexanecarboxylic acid and 87.9% 1-(2-ethyl-butyl)-cyclohexanecarboxylic acid corresponding to a yield of 72%.

EXAMPLE 4

Alkylation of CHCA Na Salt in the Presence of Diisopropylamine (1.0 eq)

CHCA Na salt (12.0 g, 80 mmol) was suspended under argon in THF (150 mL). Diisopropylamine (8.09 g, 80 mmol) was added to the stirred mixture followed by addition of 1.6 M BuLi in hexane (65 mL, 104 mmol) over 3 h using a syringe pump. After complete BuLi addition stirring at RT was continued for 1.5 h. 1-Bromo-2-ethylbutane (17.15 g, 104 mmol) in THF (51 mL) was added dropwise to the orange and slightly turbid reaction mixture at 10-15° C. over 30 min. After 1 h the reaction mixture was warmed up to 23° C. and stirred 15 h at this temperature.

At 5° C., ice-cold $H_2O$ (90 mL) was added cautiously under stirring. Then heptane and $H_2O$ was added and the mixture was concentrated in vacuo until most of the THF was removed. The aqueous residue was extracted with heptane (100 mL). The aqueous phase was separated and extracted again with heptane (100 mL). The organic phases were washed with $H_2O$. The aqueous phases were combined, adjusted to ~pH 2 with aqueous HCl and extracted with DCM (2×150 mL). The dichloromethane phases were washed with dilute brine, dried over sodium sulfate and concentrated in vacuo to give 14.35 g crude product which—by GC area %—contained 81.4% 1-(2-ethyl-butyl)-cyclohexanecarboxylic acid and 8.4% cyclohexanecarboxylic acid.

The crude product was dissolved in TBME (150 mL) and extracted with 7% aqueous sodium bicarbonate (2×80 mL). The aqueous phases were extracted with TBME. The organic phases were washed with dilute brine (120 mL), combined, dried over sodium sulfate and concentrated in vacuo to afford 12.97 g (72%) 1-(2-ethyl-butyl)-cyclohexanecarboxylic acid with a content of 93.7% according to GC with internal standard. Only a very small amount of cyclohexanecarboxylic acid (~0.1%) was detected in this product.

EXAMPLE 5

Alkylation of CHCA Na Salt in the Presence of Diisopropylamine with 1-iodo-2-ethylbutane as the Alkylating Agent CHCA Na salt (1.20 g, 8.0 mmol) in the presence of diisopropylamine (0.3 eq) and THF was reacted with 1.6 M BuLi in hexane (1.4 eq+0.3 eq) and the alkylating agent (1.3 eq) in an analogous manner as described in Example 2 except for the fact that 1-bromo-2-ethylbutane was replaced by 1-iodo-2-ethylbutane as the alkylating agent. The reaction afforded 1.35 g crude product with a content of 6% cyclohexanecarboxylic acid and 74.4% 1-(2-ethyl-butyl)-cyclohexanecarboxylic acid corresponding to a yield of 59%.

EXAMPLE 6

Alkylation of CHCA Na Salt in the Presence of Dicyclohexylamine (0.3 eq) CHCA Na Salt (2.34 g, 15.6 mmol) Was Suspended Under Argon in THF (30 mL)

Dicyclohexylamine (849 mg, 4.68 mmol) was added to the stirred mixture followed by addition of 1.6 M BuLi in hexane (13.6 mL, 21.8 mmol) over 1.5 h using a syringe pump. After complete BuLi addition stirring at RT was continued for 1.5 h. 1-Bromo-2-ethylbutane (3.35 g, 20.3 mmol) in THF (10 mL) was added dropwise to the orange and slightly turbid reaction mixture at ~0° C. over 10 min. After 1 h the cooling bath was removed and the white suspension was stirred 18 h at ambient temperature. GC analysis indicated the presence of 7% unreacted starting material.

At 5° C., ice-cold $H_2O$ (15 mL) was cautiously dropped to the reaction mixture under stirring. Then hexane and $H_2O$ were added and the mixture was concentrated in vacuo until most of the THF was removed. The residue was extracted with hexane (2×60 mL). The organic phases were washed with $H_2O$. The aqueous phases were combined, adjusted to ~pH 2 with aqueous HCl and extracted with DCM (2×100 mL). The dichloromethane phases were washed with dilute brine, dried over sodium sulfate and concentrated in vacuo to give 2.3 g crude product with a content of 6.9% cyclohexanecarboxylic acid and 87.0% 1-(2-ethyl-butyl)-cyclohexanecarboxylic acid corresponding to a yield of 60%.

EXAMPLE 7

Alkylation of CHCA Na Salt in the Presence of DEA (0.1 eq) With Supplementary BuLi Addition CHCA Na salt (6.0 g, 40 mmol) was suspended under argon in THF (75 mL). DEA (292 mg, 4 mmol) was added to the stirred mixture followed by addition of 1.6 M BuLi in hexane (30 mL, 48 mmol) over 3 h using a syringe pump. After complete BuLi addition stirring at RT was continued for 1.5 h. 1-Bromo-2-ethylbutane (8.58 g, 52 mmol) in THF (26 mL) was added dropwise to the orange and slightly turbid reaction mixture at 10° C. over 30 min. After 1 h the cooling bath was removed and the reaction mixture was stirred 17 h at ambient temperature. GC analysis indicated the presence of 12% unreacted starting material. An additional portion of 1.6 M BuLi in hexane (6.2 mL, 10 mmol) was added over 1 h to the reaction mixture and stirring at RT was continued for another 2 h.

At 5° C., ice-cold $H_2O$ (50 mL) was added cautiously under stirring. Then heptane and $H_2O$ was added and the mixture was concentrated in vacuo until most of the THF was removed. The residue was extracted with heptane. The aqueous phase was separated and extracted again with heptane. The organic phases were washed with $H_2O$. The aqueous phases were combined, adjusted to pH 1-2 with aqueous HCl and extracted twice with DCM. The dichloromethane phases were washed with dilute brine, dried over sodium sulfate and concentrated in vacuo to give 6.86 g crude product with a content of 93.6% 1-(2-ethyl-butyl)-cyclohexanecarboxylic acid and 3.7% cyclohexanecarboxylic acid.

The crude product was dissolved in TBME (60 mL) and extracted with 7% aqueous sodium bicarbonate (2×40 mL). The aqueous phases were extracted with TBME (60 mL). The organic phases were washed with dilute brine, combined, dried over sodium sulfate and concentrated in vacuo to afford 6.62 g (77%) 1-(2-ethyl-butyl)-cyclohexanecarboxylic acid with a content of 99.4% according to GC with internal standard. Only 0.2% cyclohexanecarboxylic acid (from starting material) was detected by GC analysis.

$^1$H NMR (300 MHz, $CDCl_3$) δ0.81 (t, 6H), 1.15-1.65 (m, 15H), 2.05-2.15 (m, 2H), 11.9 (br s, 1H).

EXAMPLE 8

Alkylation of CHCA Na Salt in the Presence of DEA (0.1 eq) Without Supplementary BuLi Addition CHCA Na salt (24.0 g, 160 mmol) was suspended under argon in THF (300 mL). DEA (1.17 g, 16 mmol) was added to the stirred mixture followed by addition of 1.6 M BuLi in hexane (120 mL, 192 mmol) over 3 h using a syringe pump. After complete BuLi addition stirring at RT was continued for 1.5 h. 1-Bromo-2-ethylbutane (34.29 g, 208 mmol) in THF (102 mL) was added dropwise to the orange and slightly turbid reaction mixture at 10° C. over 30 min. After 1 h the cooling bath was removed and the reaction mixture was stirred 19 h at ambient temperature. GC analysis indicated the presence of 13% unreacted starting material. In contrast to the procedure described in Example 7 no supplementary BuLi was added at this point.

The reaction mixture was worked up in analogous manner as described in Example 7 to give 28.98 g crude product with a content of 85.2% 1-(2-ethyl-butyl)-cyclohexanecarboxylic acid and 13.1% starting material.

The crude product was dissolved in TBME (100 mL) and extracted with 7% aqueous sodium bicarbonate (2×120 mL). The aqueous phases were extracted with TBME (120 mL). The organic phases were washed with dilute brine (120 mL), combined, dried over sodium sulfate and concentrated in vacuo to afford 25.17 g (73%) 1-(2-ethyl-butyl)-cyclohexanecarboxylic acid with a content of 98.2% according to GC with internal standard. The content of cyclohexanecarboxylic acid was found to be 0.3%.

EXAMPLE 9

Alkylation of CHCA Na Salt in the Presence of DEA (0.1 eq) With Tert-Butylbenzene as Co-solvent CHCA Na salt (6.0 g, 40 mmol) was suspended under argon in a mixture of THF (60 mL) and tert-butylbenzene (15 mL). DEA (292 mg, 4 mmol) was added to the stirred mixture followed by addition of 1.6 M BuLi in hexane (30 mL, 48 mmol) over 3 h using a syringe pump. After complete BuLi addition stirring at RT was continued for 1.5 h. 1-Bromo-2-ethylbutane (8.58 g, 52 mmol) in THF (26 mL) was added dropwise to the orange and slightly turbid reaction mixture at 10-15° C. over 30 min. After 1 h the cooling bath was removed and the reaction mixture was stirred 20 h at ambient temperature.

At 5° C., ice-cold $H_2O$ (30 mL) was added cautiously under stirring. Then heptane and $H_2O$ was added and the mixture was concentrated in vacuo until most of the THF was removed. The aqueous residue was extracted with heptane (80 mL). The aqueous phase was separated and extracted again with heptane (120 mL). The organic phases were washed with $H_2O$. The aqueous phases were combined, adjusted to pH 1-2 with aqueous HCl and extracted with DCM (2×150 mL). The dichloromethane phases were washed with dilute brine, dried over sodium sulfate and concentrated in vacuo to give 7.1 g crude product with a content of 82.6% 1-(2-ethyl-butyl)-cyclohexanecarboxylic acid and 9% cyclohexanecarboxylic acid.

The crude product was dissolved in TBME (70 mL) and extracted with 7% aqueous sodium bicarbonate (2×70 mL). The aqueous phases were extracted with TBME (70 mL). The organic phases were washed with dilute brine (80 mL), combined, dried over sodium sulfate and concentrated in vacuo to afford 6.36 g (71%) 1-(2-ethyl-butyl)-cyclohexanecarboxylic acid with a content of 95.3% according to GC with internal standard. Only a very small amount of cyclohexanecarboxylic acid (~0.1%) was detected in this product.

EXAMPLE 10

Alkylation in the Presence of DEA (0.1 eq) With in situ Generation of the CHCA Na Salt At 0° C., cyclohexanecarboxylic acid (2.0 g, 15.6 mmol) in THF (15 mL) was added dropwise over 30 min under an argon atmosphere to a stirred suspension of 60% sodium hydride in oil (811 mg, 20.3 mmol). After another 10 min at 0° C., the suspension was stirred at RT for 40 min.

DEA (114 mg, 1.56 mmol) was added to the stirred mixture followed by addition of 1.6 M BuLi in hexane (11.7 mL, 18.7 mmol) over 3 h using a syringe pump. After complete BuLi addition stirring at RT was continued for 1 h. 1-Bromo-2-ethylbutane (3.35 g, 20.3 mmol) in THF (10 mL) was added dropwise to the orange and slightly turbid reaction mixture at 0° C. over 10 min. After 1 h the cooling bath was removed and the reaction mixture was stirred 18 h at ambient temperature. GC analysis indicated the presence of 11% unreacted starting material. An additional portion of 1.6 M BuLi in hexane (1.95 mL, 3.12 mmol) was added over 1 h to the reaction mixture and stirring at RT was continued for 1 h.

At 5° C., ice-cold $H_2O$ (15 mL) was cautiously dropped to the reaction mixture under stirring. Then heptane and $H_2O$ were added and the mixture was concentrated in vacuo until most of the THF was removed. The residue was extracted with heptane (2×60 mL). The organic phases were washed with $H_2O$. The aqueous phases were combined, adjusted to <pH 3 with aqueous HCl and extracted with DCM (2×100 mL). The dichloromethane phases were washed with dilute brine, dried over sodium sulfate and concentrated in vacuo to give 2.75 g crude product with a content of 3.7% cyclohexanecarboxylic acid and 87.6% 1-(2-ethyl-butyl)-cyclohexanecarboxylic acid corresponding to a yield of 73%.

EXAMPLE 11

Preparation of Cyclohexanecarboxylic Acid Lithium Salt

Under stirring, a solution of cyclohexanecarboxylic acid (10.0 g, 78 mmol) in MeOH (30 mL) was added dropwise over 30 min to 1 M lithium methoxide in MeOH (78 mL, 78 mmol) at 5-10° C. The cooling bath was removed and after 4 h at room temperature, heptane (75 mL) was added slowly. Most of the MeOH was removed at a rotary evaporator. Heptane (100 mL) was added to the thick white suspension which was stirred 2 h at 0° C. The suspension was filtered and the filter cake was washed with heptane and dried in vacuo (<1 mbar) to afford 10.5 g (100%) cyclohexanecarboxylic acid lithium salt. Anal. Calcd for $C_7H_{11}LiO_2$ C, 62.70; H, 8.27. Found: C, 62.03; H, 8.11; $H_2O$, 0.67.

EXAMPLE 12

Alkylation of CHCA Li Salt in the Presence of DEA (0.1 eq)

Cyclohexanecarboxylic acid lithium salt (6.0 g, 44.7 mmol, preparation see Example 11) was suspended under argon in THF (75 mL). DEA (327 mg, 4.47 mmol) was added to the stirred mixture followed by addition of 1.6 M BuLi in hexane (33.6 mL, 53.7 mmol) over 3 h using a syringe pump. After complete BuLi addition stirring at RT was continued for 1.5 h. 1-Bromo-2-ethylbutane (9.6 g, 58.2 mmol) in THF (26 mL) was added dropwise to the orange and slightly turbid reaction mixture at 10-15° C. over 30 min. After 1 h the cooling bath was removed and the white suspension was stirred 18 h at ambient temperature.

At 5° C., ice-cold $H_2O$ (30 mL) was cautiously dropped to the reaction mixture under stirring. Then hexane and $H_2O$ were added and the mixture was concentrated in vacuo until most of the THF was removed. The residue was extracted with hexane (80+120 mL). The organic phases were washed with $H_2O$. The aqueous phases were combined, adjusted to ~pH 2 with aqueous HCl and extracted with DCM (2×150 mL). The dichloromethane phases were washed with dilute brine, dried over sodium sulfate and concentrated in vacuo to give 6.75 g crude product with a content of 27.7% cyclohexanecarboxylic acid and 68.3% 1-(2-ethyl-butyl)-cyclohexanecarboxylic acid corresponding to a yield of 49%.

EXAMPLE 13

Alkylation of CHCA Na Salt in the Presence of DEA (0.1 eq)

CHCA Na salt (45.0 g, 300 mmol) was suspended under argon in THF (420 mL). DEA (2.2 g, 30 mmol) was added to the stirred mixture followed by addition of 1.6 M BuLi in hexane (225 mL, 360 mmol) over 4 h at 20-25° C. After complete BuLi addition the reaction mixture was cooled to 10° C. and 1-bromo-2-ethylbutane (60.0 g, 360 mmol) was added at 8-12° C. over 30 min. After complete addition the reaction mixture was warmed to 35° C. within 30 min and stirred for 19 h at 33-37° C. GC analysis indicated the presence of 10.8% area unreacted starting material (cyclohexanecarboxylic acid).

The reaction mixture was cooled to 0-5° C. and $H_2O$ (400 mL) was added within 10-20 min at 0-15° C. Volatile components (THF, hexanes, etc) were distilled at 45° C./400-100 mbar. The remaining basic aqueous solution was washed twice with hexanes (240 and 120 mL) and acidified by addition of HCl 37% (35 mL) at 0-15° C. The acidic aqueous solution was extracted with toluene (240 mL) and the organic phase was washed with $H_2O$ (240 mL).

The toluene solution with the crude product was extracted 3 times (150 mL each) with 7% aqueous sodium bicarbonate (set to pH=9 by addition of 28% NaOH) and once with HCl 0.5N (50 mL). The organic phase was concentrated in vacuo to afford 51.8 g (78.8% yield) 1-(2-ethyl-butyl)-cyclohexanecarboxylic acid with a content of 96.9% according to GC with internal standard. The content of toluene was found to be 3.7% and of cyclohexanecarboxylic acid was found to be <0.1%.

EXAMPLE 14

Alkylation of CHCA Na Salt as in Example 13 but With Aging Time of Dianion Solution (90 min) and With Alkylation Temperature of 20-25° C.

CHCA Na salt (45.0 g, 300 mmol) was suspended under argon in THF (420 mL). DEA (2.2 g, 30 mmol) was added to the stirred mixture followed by addition of 1.6 M BuLi in hexane (225 mL, 360 mmol) over 4 h at 20-25° C. After complete BuLi addition the reaction mixture was stirred for further 90 min at 20-25° C., then cooled to 10° C. and 1-bromo-2-ethylbutane (60.0 g, 360 mmol) was added at 8-12° C. over 30 min. After complete addition the reaction mixture was stirred for additional 60 min at 10-12° C. and then warmed to 20-25° C. within 30 min and stirred for 16.5 h at 20-25° C. GC analysis indicated the presence of 7.7% area unreacted starting material (cyclohexanecarboxylic acid).

The reaction mixture was cooled to 0-5° C. and $H_2O$ (400 mL) was added within 10-20 min at 0-15° C. Volatile components (THF, hexanes, etc) were distilled at 45° C./400-100 mbar. The remaining basic aqueous solution was washed twice with hexanes (240 and 120 mL) and acidified by addition of HCl 37% (33 mL) at 0-15° C. The acidic aqueous solution was extracted with toluene (240 mL) and the organic phase was washed with $H_2O$ (240 mL).

The toluene solution with the crude product (89.0% area 1-(2-ethyl-butyl)-cyclohexane-carboxylic acid and 9.5% area cyclohexanecarboxylic acid) was extracted 3 times (150 mL each) with 7% aqueous sodium bicarbonate (set to pH=9 by addition of 28% NaOH) and once with HCl 0.5N (50 mL). The organic phase was concentrated in vacuo to afford 50.2 g (76.0% yield) 1-(2-ethyl-butyl)-cyclohexanecarboxylic acid with a content of 94.5% according to GC with internal standard. The content of toluene was found to be 3.4% and of cyclohexanecarboxylic acid was found to be <0.1%.

EXAMPLE 15

Alkylation of CHCA Na Salt as in Example 14 but With Reduced Dosing Time of BuLi (1.5 h) and With 1.3 Eq. of 1-bromo-2-ethylbutane. Basic Aqueous Solution was Extracted Only Once With Hexanes. Extractive Purification With 7% Sodium Bicarbonate CHCA Na salt (45.0 g, 300 mmol) was suspended under argon in THF (420 mL). DEA (2.2 g, 30 mmol) was added to the stirred mixture followed by addition of 1.6 M BuLi in hexane (225 mL, 360 mmol) over 90 min at 20-25° C. After complete BuLi addition the reaction mixture was stirred for further 90 min at 20-25° C., then cooled to 10° C. and 1-bromo-2-ethylbutane (65.0 g, 390 mmol) was added at 8-12° C. over 30 min. After complete addition the reaction mixture was warmed to 20-25° C. within 30 min and stirred for 20 h at 20-25° C. GC analysis indicated the presence of 9.3% area unreacted starting material (cyclohexanecarboxylic acid).

The reaction mixture was cooled to 0-5° C. and $H_2O$ (400 mL) was added within 5 min at 0-15° C. Volatile components (THF, hexanes, etc) were distilled at 45° C./400-100 mbar. The remaining basic aqueous solution was washed with hexanes (240 mL) and acidified by addition of HCl 37% (38 mL) at 10-15° C. The acidic aqueous solution was extracted with toluene (240 mL). The organic phase was washed with $H_2O$ (240 mL) and concentrated in vacuo.

The residue was dissolved in toluene (220 mL) and the solution with the crude product was extracted 3 times (150 mL each) with 7% aqueous sodium bicarbonate and once with HCl 0.29N (140 mL). The organic phase was concentrated in vacuo to afford 42.0 g (61.7.0% yield) 1-(2-ethyl-butyl)-cyclohexanecarboxylic acid with a content of 92.3% according to GC with internal standard. The content of toluene was found to be 4.5% and of cyclohexanecarboxylic acid was found to be <0.1%.

EXAMPLE 16

Alkylation of CHCA Na Salt as in Example 15 but With 0.2 Eq. of Diethylamine and 3 h Dosing Time of BuLi. Extractive Purification With 7% Sodium Bicarbonate CHCA Na salt (45.0 g, 300 mmol) was suspended under argon in THF (420 mL). DEA (4.4 g, 60 mmol) was added to the stirred mixture followed by addition of 1.6 M BuLi in hexane (225 mL, 360 mmol) over 3 h at 20-25° C. After complete BuLi addition the reaction mixture was stirred for further 90 min at 20-25° C., then cooled to 10° C. and 1-bromo-2-ethylbutane (65.0 g, 390 mmol) was added at 8-12° C. over 30 min. After complete addition the reaction mixture was stirred for 1 h at 8-12° C., then warmed to 20-25° C. within 30 min and stirred for 19 h at 20-25° C. GC analysis indicated the presence of 13.7% area unreacted starting material (cyclohexanecarboxylic acid).

The reaction mixture was cooled to 0-5° C. and $H_2O$ (400 mL) was added within 5 min at 0-15° C. Volatile components (THF, hexanes, etc) were distilled at 45° C./400-100 mbar. The remaining basic aqueous solution was washed with hexanes (240 mL) and acidified by addition of HCl 37% (38 mL) at 10-15° C. The acidic aqueous solution was extracted with toluene (240 mL). The organic phase was washed with $H_2O$ (240 mL) and concentrated in vacuo.

The residue was dissolved in toluene (220 mL) and the solution with the crude product was extracted 2 times (150 mL each) with 7% aqueous sodium bicarbonate and once with 5% NaCl (55 mL). The organic phase was concentrated in vacuo to afford 45.2 g (65.6% yield) 1-(2-ethyl-butyl)-cyclohexanecarboxylic acid with a content of 88.5% according to GC with internal standard. The content of toluene was found to be 5.3% and of cyclohexanecarboxylic acid was found to be 4.3%.

EXAMPLE 17

Alkylation of CHCA Na Salt with 0.1 Eq. of Diethylamine, 1.1 Eq. of BuLi, 1.2 Eq. of 1-bromo-2-ethylbutane and 3 h Dosing Time of BuLi. Basic Aqueous Extraction With TBME. Extractive Purification With Either 7% Sodium Bicarbonate or 7% Sodium Phosphate (set to pH=8.5 With Phosphoric Acid)

CHCA Na salt (45.0 g, 300 mmol) was suspended under argon in THF (420 mL). DEA (2.2 g, 30 mmol) was added to the stirred mixture followed by addition of 1.6 M BuLi in hexane (206 mL, 330 mmol) over 3 h at 20-25° C. After complete BuLi addition the reaction mixture was stirred for further 90 min at 20-25° C., then cooled to 10° C. and 1-bromo-2-ethylbutane (60.0 g, 360 mmol) was added at 8-12° C. over 30 min. After complete addition the reaction mixture was stirred for 1 h at 8-12° C., then warmed to 20-25° C. within 30 min and stirred for 19 h at 20-25° C. GC analysis indicated the presence of 18.4% area unreacted starting material (cyclohexanecarboxylic acid).

The reaction mixture was cooled to 0-5° C. and $H_2O$ (400 mL) was added within 5 min at 0-15° C. Volatile components (THF, hexanes, etc) were distilled at 45° C./400-100 mbar. The remaining basic aqueous solution was washed with TBME (240 mL) resulting in a 3 layer system. The lower 2 layers were acidified by addition of HCl 37% (38 mL) at 10-15° C. The acidic aqueous solution was extracted with toluene (240 mL). The organic phase was washed with $H_2O$ (240 mL) and concentrated in vacuo. The residue (50.4 g), which contained 66.4% of 1-(2-ethyl-butyl)-cyclohexanecarboxylic acid and 27.3% of cyclohexanecarboxylic acid was divided in 2 equal parts.

25.2 g of the crude residue were dissolved in toluene (110 mL). Then, the toluene solution was extracted 3 times (75 mL each) with 7% aqueous sodium bicarbonate and once with $H_2O$ (50 mL). The organic phase was concentrated in vacuo to afford 17.5 g (52.0% yield) 1-(2-ethyl-butyl)-cyclohexanecarboxylic acid with a content of 93.9% according to GC with internal standard. The content of toluene was found to be 3.8% and of cyclohexanecarboxylic acid was found to be 0.33%.

The second part of the crude residue (25.2 g) was dissolved in 110 mL toluene. Then, the toluene solution was extracted twice (75 mL each) with 7% aqueous sodium phosphate (set to pH=8.5 with $H_3PO_4$). The organic phase was concentrated in vacuo to afford 20.0 g (52.8% yield) 1-(2-ethyl-butyl)-cyclohexanecarboxylic acid with a content of 83.5% according to GC with internal standard. The content of toluene was found to be 3.0% and of cyclohexanecarboxylic acid was found to be 10.6%.

EXAMPLE 18

Alkylation of CHCA Na Salt With 0.1 Eq. of Diethylamine, 1.2 Eq. of BuLi, 1.2 Eq. of 1-bromo-2-ethylbutane and 3.5 h Dosing Time of BuLi. Addition of BuLi Performed at 35° C.

CHCA Na salt (45.0 g, 300 mmol) was suspended under argon in THF (420 mL). DEA (2.2 g, 30 mmol) was added to the stirred mixture followed by addition of 1.6 M BuLi in hexane (225 mL, 360 mmol) over 3.5 h at 35° C. After complete BuLi addition the reaction mixture was stirred for further 90 min at 35° C., then cooled to 10° C. and 1-bromo-2-ethylbutane (60.0 g, 360 mmol) was added at 8-12° C. over 30 min. After complete addition the reaction mixture was stirred for 1 h at 8-12° C., then warmed to 20-25° C. within 30 min and stirred for 19 h at 20-25° C. GC analysis indicated the presence of 12.7% area unreacted starting material (cyclohexanecarboxylic acid).

The reaction mixture was cooled to 0-5° C. and $H_2O$ (400 mL) was added within 5 min at 0-15° C. Volatile components (THF, hexanes, etc) were distilled at 45° C./400-100 mbar. The remaining basic aqueous solution was washed with hexanes (240 mL and 120 mL) and acidified by addition of HCl 37% (38 mL) at 10-15° C. The acidic aqueous solution was extracted with toluene (240 mL). The organic phase was washed with $H_2O$ (240 mL).

The toluene solution with the crude product (83.7% area 1-(2-ethyl-butyl)-cyclohexane-carboxylic acid and 15.2% area cyclohexanecarboxylic acid) was extracted 3 times (150 mL each) with 7% aqueous sodium bicarbonate (set to pH=9 by addition of 28% NaOH) and once with 1N HCl (100 mL). The organic phase was concentrated in vacuo to afford 46.5 g (69.6% yield) 1-(2-ethyl-butyl)-cyclohexanecarboxylic acid with a content of 95.3% according to GC with internal standard. The content of toluene was found to be 3.9% and of cyclohexanecarboxylic acid was found to be <0.10%.

EXAMPLE 19

Alkylation of CHCA Na Salt With 0.1 Eq. of Diethylamine, 1.2 Eq. of BuLi, 1.2 Eq. of 1-bromo-2-ethylbutane and 3 h Dosing Time of BuLi. Addition of BuLi Performed at 30° C. and 3 h Stirring of Dianion Solution CHCA Na salt (45.0 g, 300 mmol) was suspended under argon in THF (420 mL). DEA (2.2 g, 30 mmol) was added to the stirred mixture followed by addition of 1.6 M BuLi in hexane (225 mL, 360 mmol) over 3 h at 30° C. After complete BuLi addition the reaction mixture was stirred for further 3 h at 30° C., then cooled to 10° C. and 1-bromo-2-ethylbutane (60.0 g, 360 mmol) was added at 8-12° C. over 30 min. After complete addition the reaction mixture was stirred for 1 h at 8-12° C., then warmed to 20-25° C. within 30 min and stirred for 17 h at 20-25° C. GC analysis indicated the presence of 17.4% area unreacted starting material (cyclohexanecarboxylic acid).

The reaction mixture was cooled to 0-5° C. and $H_2O$ (400 mL) was added within 5 min at 0-15° C. Volatile components (THF, hexanes, etc) were distilled at 45° C./400-100 mbar. The remaining basic aqueous solution was washed with hexanes (240 mL and 120 mL) and acidified by addition of HCl 37% (38 mL) at 10-15° C. The acidic aqueous solution was extracted with toluene (240 mL). The organic phase was washed with $H_2O$ (240 mL).

The toluene solution with the crude product (77.8% area 1-(2-ethyl-butyl)-cyclohexane-carboxylic acid and 21.5% area cyclohexanecarboxylic acid) was extracted 3 times (150 mL each) with 7% aqueous sodium bicarbonate (set to pH=9 by addition of 28% NaOH) and once with 1N HCl (50 mL). The organic phase was concentrated in vacuo to afford 41.4 g (62.3% yield) 1-(2-ethyl-butyl)-cyclohexanecarboxylic acid with a content of 95.8% according to GC with internal standard. The content of toluene was found to be 3.0% and of cyclohexanecarboxylic acid was found to be <0.10%.

EXAMPLE 20

Alkylation of CHCA Na Salt as in Example 14 but With 3 h Dosing Time of BuLi and Use of 2.5M BuLi CHCA Na salt (45.0 g, 300 mmol) was suspended under argon in THF (420 mL). DEA (2.2 g, 30 mmol) was added to the stirred mixture followed by addition of 2.5 M BuLi in hexane (144 mL, 360 mmol) over 3 h at 20-25° C. After complete BuLi addition the reaction mixture was stirred for further 90 min at 20-25° C., then cooled to 10° C. and 1-bromo-2-ethylbutane (60.0 g, 360 mmol) was added at 8-12° C. over 30 min. After complete addition the reaction mixture was stirred for additional 60 min at 10-12° C. and then warmed to 20-25° C. within 30 min and stirred for 18.5 h at 20-25° C. GC analysis indicated the presence of 19.9% area unreacted starting material (cyclohexanecarboxylic acid).

The reaction mixture was cooled to 0-5° C. and $H_2O$ (400 mL) was added within 10-20 min at 0-15° C. Volatile components (THF, hexanes, etc) were distilled at 45° C./400-100 mbar. The remaining basic aqueous solution was washed twice with hexanes (240 and 120 mL) and acidified by addition of HCl 37% (38 mL) at 0-15° C. The acidic aqueous solution was extracted with toluene (240 mL) and the organic phase was washed with $H_2O$ (240 mL).

The toluene solution with the crude product (73.7% area 1-(2-ethyl-butyl)-cyclohexane-carboxylic acid and 25.7% area cyclohexanecarboxylic acid) was extracted 3 times (150 mL each) with 7% aqueous sodium bicarbonate (set to pH=9 by addition of 28% NaOH) and once with HCl 0.5N (50 mL). The organic phase was concentrated in vacuo to afford 35.4 g (54.6% yield) 1-(2-ethyl-butyl)-cyclohexanecarboxylic acid with a content of 98.4% according to GC with internal standard. The content of toluene was found to be 1.7% and of cyclohexanecarboxylic acid was found to be 0.11%.

EXAMPLE 21

Alkylation of CHCA Na Salt in the Presence of DEA (0.1 eq) With toluene-4-sulfonic Acid 2-ethyl-butyl Ester as the Alkylating Agent CHCA Na salt (3.0 g, 20 mmol) was suspended under argon in THF (37.5 mL). DEA (146 mg, 2 mmol) was added to the stirred mixture followed by addition of 1.6 M BuLi in hexane (15 mL, 24 mmol) over 3 h using a syringe pump. After complete BuLi addition stirring at RT was continued for 1.5 h. Toluene-4-sulfonic acid 2-ethyl-butyl ester (6.66 g, 26 mmol) in THF (13 mL) was added dropwise to the orange and slightly turbid reaction mixture at 10° C. over 30 min. After 1 h the cooling bath was removed and the reaction mixture was stirred 18 h at ambient temperature.

The reaction mixture was worked up in analogous manner as described in Example 7 to give 3.2 g crude product with a content of 57% 1-(2-ethyl-butyl)-cyclohexanecarboxylic acid and 29.5% starting material.

The crude product was dissolved in TBME (30 mL) and extracted with 7% aqueous sodium bicarbonate (2×30 mL). The aqueous phases were extracted with TBME (40 mL). The organic phases were washed with dilute brine (50 mL), combined, dried over sodium sulfate and concentrated in vacuo. This extraction procedure was repeated to afford 1.79 g (37%) 1-(2-ethyl-butyl)-cyclohexanecarboxylic acid with a content of 87.7% according to GC with internal standard. The content of cyclohexanecarboxylic acid was found to be <0.1%.

EXAMPLE 22

Alkylation of CHCA Na Salt in the Presence of Morpholine as the Secondary Amine

CHCA Na salt (3.0 g, 20 mmol) was suspended under argon in THF (37.5 mL). Morpholine (174 mg, 2 mmol) was added to the stirred mixture followed by addition of 1.6 M BuLi in hexane (15 mL, 24 mmol) over 3 h using a syringe pump. After complete BuLi addition stirring at RT was continued for 1.5 h. 1-Bromo-2-ethylbutane (4.29 g, 26 mmol) in THF (13 mL) was added dropwise to the orange and slightly turbid reaction mixture at 10° C. over 30 min. After 1 h the cooling bath was removed and the reaction mixture was stirred 18 h at ambient temperature.

The reaction mixture was worked up in analogous manner as described in Example 7 to give 4.16 g crude product with a content of 20.5% cyclohexanecarboxylic acid and 74.5% 1-(2-ethyl-butyl)-cyclohexanecarboxylic acid corresponding to a yield of 73%.

EXAMPLE 23

Alkylation of CHCA Na Salt in the Presence of Pyrrolidine as the Secondary Amine CHCA Na salt (3.0 g, 20 mmol) was suspended under argon in THF (37.5 mL). Pyrrolidine (142 mg, 2 mmol) was added to the stirred mixture followed by addition of 1.6 M BuLi in hexane (15 mL, 24 mmol) over 3 h using a syringe pump. After complete BuLi addition stirring at RT was continued for 1.5 h. 1-Bromo-2-ethylbutane (4.29 g, 26 mmol) in THF (13 mL) was added dropwise to the orange and slightly turbid reaction mixture at 10° C. over 30 min. After 1 h the cooling bath was removed and the reaction mixture was stirred 18 h at ambient temperature.

The reaction mixture was worked up in analogous manner as described in Example 7 to give 3.92 g crude product with a content of 30% cyclohexanecarboxylic acid and 65.1% 1-(2-ethyl-butyl)-cyclohexanecarboxylic acid corresponding to a yield of 60%.

EXAMPLE 24

Alkylation of CHCA Na Salt in the Presence of 4-methylpiperidine as the Secondary Amine CHCA Na salt (3.0 g, 20 mmol) was suspended under argon in THF (37.5 mL). 4-Methylpiperidine (198 mg, 2 mmol) was added to the stirred mixture followed by addition of 1.6 M BuLi in hexane (15 mL, 24 mmol) over 3 h using a syringe pump. After complete BuLi addition stirring at RT was continued for 1.5 h. 1-Bromo-2-ethylbutane (4.29 g, 26 mmol) in THF (13 mL) was added dropwise to the orange and slightly turbid reaction mixture at 10 ° C. over 30 min. After 1 h the cooling bath was removed and the reaction mixture was stirred 18 h at ambient temperature.

The reaction mixture was worked up in analogous manner as described in Example 7 to give 3.73 g crude product with a content of 28.8% cyclohexanecarboxylic acid and 69.6% 1-(2-ethyl-butyl)-cyclohexanecarboxylic acid corresponding to a yield of 61%.

EXAMPLE 25

Alkylation of CHCA Na Salt Using Phenyllithium as a Reagent

CHCA Na salt (3.0 g, 20 mmol) was suspended under argon in THF (37 mL). DEA (146 mg, 2 mmol) was added to the stirred mixture followed by addition of 1.9 M PhLi in hexane (12.6 mL, 24 mmol) over 3 h using a syringe pump. After complete PhLi addition stirring at RT was continued for 1.5 h. 1-Bromo-2-ethylbutane (4.29 g, 26 mmol) in THF (13 mL) was added dropwise to the slightly turbid reaction mixture at 10° C. over 30 min. After 1 h the cooling bath was removed and the reaction mixture was stirred 18 h at ambient temperature.

The reaction mixture was worked up in analogous manner as described in Example 7 to give 3.59 g crude product with a content of 36.4% cyclohexanecarboxylic acid and 60.7% 1-(2-ethyl-butyl)-cyclohexanecarboxylic acid corresponding to a yield of 51%.

The invention claimed is:

1. A process for the preparation of the 1-(2-ethyl-butyl)-cyclohexanecarboxylic acid of formula (I):

(I)

which comprises reacting the cyclohexanecarboxylic acid derivative of formula (II):

(II)

wherein Y is an alkali metal, with an alkylating agent, in the presence of: (1) a secondary amine and (2) a ($C_1$-$C_6$) alkyllithium, a ($C_3$-$C_6$)cycloalkyllithium, or phenyllithium.

2. The process according to claim 1 for the preparation of the 1-(2-ethyl-butyl)-cyclohexanecarboxylic acid of formula (I):

(I)

which comprises the following steps:
a) alkylating a cyclohexanecarboxylic acid derivative of formula (II):

(II)

wherein Y is an alkali metal, with an alkylating agent, in the presence of (1) a secondary amine and (2) a ($C_1$-$C_6$) alkyllithium, a ($C_3$-$C_6$)cycloalkyllithium, or phenyllithium, and b) purifying of the compound of formula (I) by extraction in the presence of an aqueous solution with a pH in the range of 7.5-11.

3. The process according claim 1, which further comprises the preparation of a cyclohexanecarboxylic acid sodium salt of formula (II):

(II)

wherein Y is an alkali metal, by reacting cyclohexanecarboxylic acid with a basic alkali metal compound.

4. The process according to claim 1, wherein the ($C_1$-$C_6$) alkyllithium, ($C_3$-$C_6$)cycloalkyllithium or phenyllithium is added first to the cyclohexanecarboxylic acid alkali salt of formula (II) in the presence of a secondary amine, followed by the addition of an alkylating agent.

5. The process according to claim 1, wherein the alkylating step is performed in the presence of an organic solvent.

6. The process according to claim 5 wherein the organic solvent is a nonprotic solvent.

7. The process according to claim 6 wherein the nonprotic solvent is tetrahydrofuran.

8. The process according to claim 1 wherein there is a catalytic amount of the secondary amine.

9. The process according to claim 1, wherein the secondary amine is diethylamine.

10. The process according to claim 3, wherein the basic alkali metal compound used is sodium methoxide.

11. The process according to claim 3, wherein the basic alkali metal compound used is sodium hydride.

12. The process according to claim 1, wherein the alkali metal is sodium.

13. The process according to claim 1, wherein the alkylating agent is 1-bromo-2-ethylbutane.

14. The process according to claim 2, wherein the aqueous solution has a pH of 9.

15. The process according to claim 1, wherein the ($C_1$-$C_6$) alkyllithium is butyllithium.

16. A process for the preparation of S-[2-([[1-(2-ethylbutyl)-cyclohexyl]-carbonyl]amino)phenyl]2-methylpropanethioate comprising the formation of a compound of formula (I):

(I)

by reacting a cyclohexanecarboxylic acid derivative of formula (II):

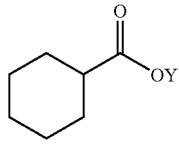
(II)

wherein Y is an alkali metal, with an alkylating agent, in the presence of: (1) a secondary amine and (2) ($C_1$-$C_6$) alkyllithium, ($C_3$-$C_6$)cycloalkyllithium, or phenyllithium.

17. A process for the preparation of a compound of formula (V) or (VI):

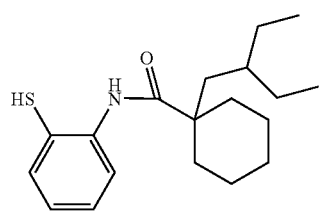
(V)

or

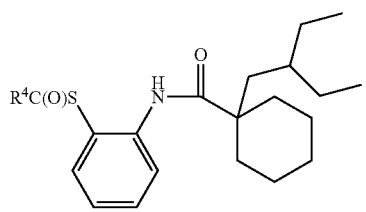
(VI)

comprising the steps of:

(1) halogenating the compound of formula (I) prepared by the process of claim 1, to obtain a compound of formula (III), wherein X is I, Br, Cl or F:

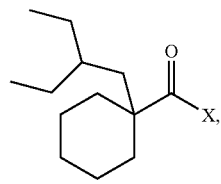
(III)

(2) acylating a compound of formula (IV'):

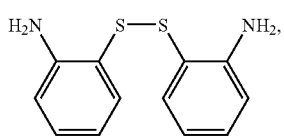
(IV')

with the compound of formula (III) to obtain a compound of formula (IV):

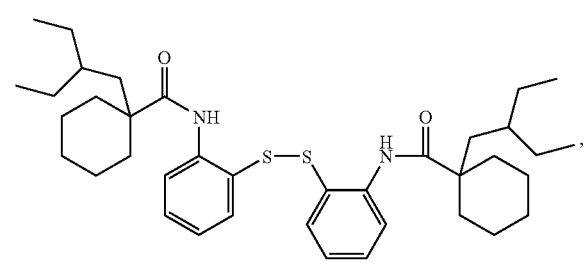
(IV)

(3) reducing the compound of formula (IV) to obtain a compound of formula (V):

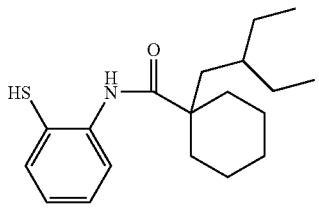
(V)

, and (4) optionally acylating the compound of formula (V) with $R^4C(O)X'$, wherein X' is I, Br, Cl or F and $R^4$ is $C_1$-$C_8$alkyl, to obtain a compound of formula (VI):

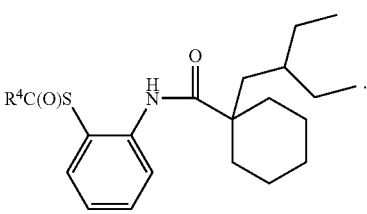
(VI)

* * * * *

UNITED STATES PATENT AND TRADEMARK OFFICE
CERTIFICATE OF CORRECTION

| | | |
|---|---|---|
| PATENT NO. | : 7,863,474 B2 | Page 1 of 1 |
| APPLICATION NO. | : 12/474328 | |
| DATED | : January 4, 2011 | |
| INVENTOR(S) | : Ursula Hoffmann and Bruno Lohri | |

It is certified that error appears in the above-identified patent and that said Letters Patent is hereby corrected as shown below:

Claim 3, column 20, line 4, after "The process according" insert -- to --

Signed and Sealed this
Twenty-second Day of March, 2011

David J. Kappos
*Director of the United States Patent and Trademark Office*